(12) United States Patent
Doyle

(10) Patent No.: US 8,900,200 B2
(45) Date of Patent: Dec. 2, 2014

(54) SYRINGE WITH NEEDLE GUARD INJECTION DEVICE

(75) Inventor: Mark Christopher Doyle, Del Mar, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 20 days.

(21) Appl. No.: 13/585,767

(22) Filed: Aug. 14, 2012

(65) Prior Publication Data

US 2012/0310207 A1     Dec. 6, 2012

Related U.S. Application Data

(63) Continuation of application No. 12/938,252, filed on Nov. 2, 2010, now Pat. No. 8,241,255, which is a continuation of application No. 11/028,902, filed on Jan. 3, 2005, now Pat. No. 7,824,379, which is a continuation of application No. 10/113,537, filed on Mar. 27, 2002, now Pat. No. 6,976,976.

(51) Int. Cl.
*A61M 5/32*     (2006.01)
*A61M 5/31*     (2006.01)

(52) U.S. Cl.
CPC ....... *A61M 5/326* (2013.01); *A61M 2005/3247* (2013.01); *A61M 5/3137* (2013.01); *A61M 5/3271* (2013.01); *A61M 2005/3264* (2013.01); *A61M 2005/3261* (2013.01); *Y10S 128/919* (2013.01)
USPC ........... 604/198; 604/110; 604/192; 604/195; 604/197; 604/221; 128/919

(58) Field of Classification Search
CPC ... A61M 5/322; A61M 5/3202; A61M 5/326; A61M 5/3271; A61M 5/315; A61M 2005/3128

USPC ......... 604/110, 192, 197, 198, 182, 195, 221, 604/227
See application file for complete search history.

(56) References Cited

U.S. PATENT DOCUMENTS

| | | | |
|---|---|---|---|
| 3,046,985 A | 7/1962 | Saenz |
| 3,702,608 A | 11/1972 | Tibbs |
| 3,890,971 A | 6/1975 | Leeson et al. |
| 4,927,416 A | 5/1990 | Tomkiel |
| 4,969,877 A | 11/1990 | Kornberg |
| 5,057,087 A | 10/1991 | Harmon |
| 5,193,552 A | 3/1993 | Columbus et al. |

(Continued)

FOREIGN PATENT DOCUMENTS

EP        0 680 767 A1    11/1995
WO       WO 01/85239 A2    11/2001

*Primary Examiner* — Scott Medway
(74) *Attorney, Agent, or Firm* — One LLP

(57) ABSTRACT

The present invention provides for an injection device including a syringe with a proximal end, a distal end, a needle extending from the distal end, and a plunger inserted into the proximal end. A guard is slidable on the syringe, has a proximal end, a distal end, and is biased from a first position wherein the needle is exposed towards a second position wherein the guard covers the needle. The injection device includes first and second sets of cooperating detents for retaining the guard and syringe in the first and second positions, respectively. A latch member extends proximally from the guard that is engageable by the plunger as the plunger is depressed to release the first set of cooperating detents. Upon release, a spring element biases the guard towards the second position until the second set of cooperating detents engage and secure the guard in the second position.

8 Claims, 7 Drawing Sheets

(56) References Cited

U.S. PATENT DOCUMENTS

| | | |
|---|---|---|
| 5,242,416 A | 9/1993 | Hutson |
| 5,273,541 A | 12/1993 | Malenchek |
| 5,328,485 A | 7/1994 | Moreno et al. |
| 5,385,551 A | 1/1995 | Shaw |
| 5,423,758 A | 6/1995 | Shaw |
| 5,437,647 A | 8/1995 | Firth et al. |
| 5,492,536 A | 2/1996 | Mascia |
| 5,562,624 A | 10/1996 | Righi et al. |
| 5,562,626 A | 10/1996 | Sanpietro |
| 5,571,089 A | 11/1996 | Crocker |
| 5,573,508 A | 11/1996 | Thornton |
| 5,573,513 A | 11/1996 | Wozencroft |
| 5,575,771 A | 11/1996 | Walinsky |
| 5,624,400 A | 4/1997 | Firth et al. |
| 5,716,340 A | 2/1998 | Schweich, Jr. et al. |
| 6,004,296 A | 12/1999 | Jansen et al. |
| 6,015,402 A | 1/2000 | Sahota |
| 6,030,366 A | 2/2000 | Mitchell |
| 6,102,893 A | 8/2000 | Aneas |
| 6,159,184 A | 12/2000 | Perez et al. |
| 6,171,283 B1 | 1/2001 | Perez et al. |
| 6,206,853 B1 | 3/2001 | Bonnet |
| 6,319,234 B1 | 11/2001 | Restelli et al. |
| 6,613,022 B1 | 9/2003 | Doyle |
| 6,623,459 B1 | 9/2003 | Doyle |
| 6,905,478 B2 | 6/2005 | Ingram et al. |
| 6,976,976 B2 | 12/2005 | Doyle |
| 2002/0032412 A1 | 3/2002 | Riemelmoser |
| 2003/0187402 A1 | 10/2003 | Doyle |
| 2005/0119624 A1 | 6/2005 | Doyle |

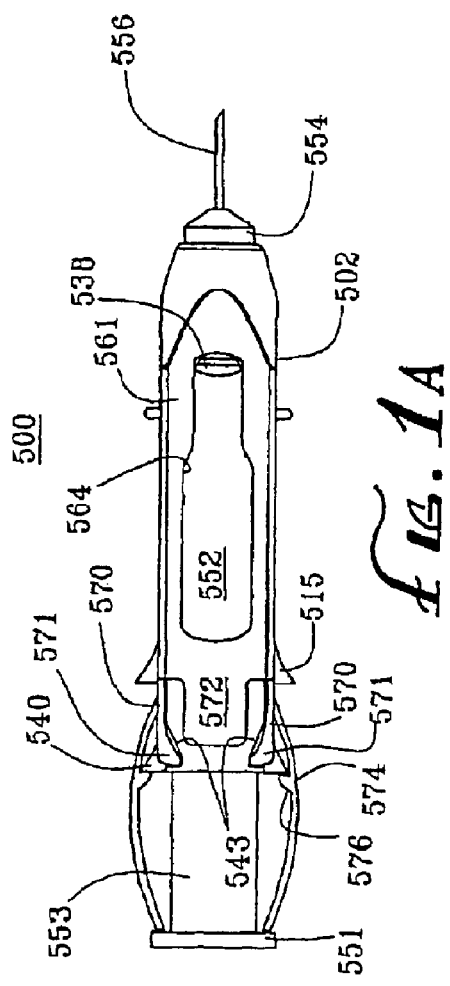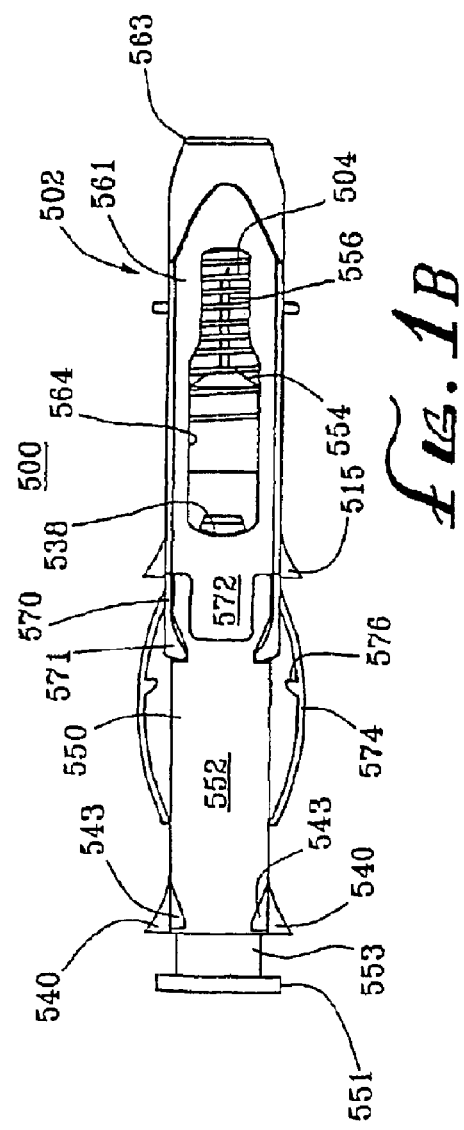

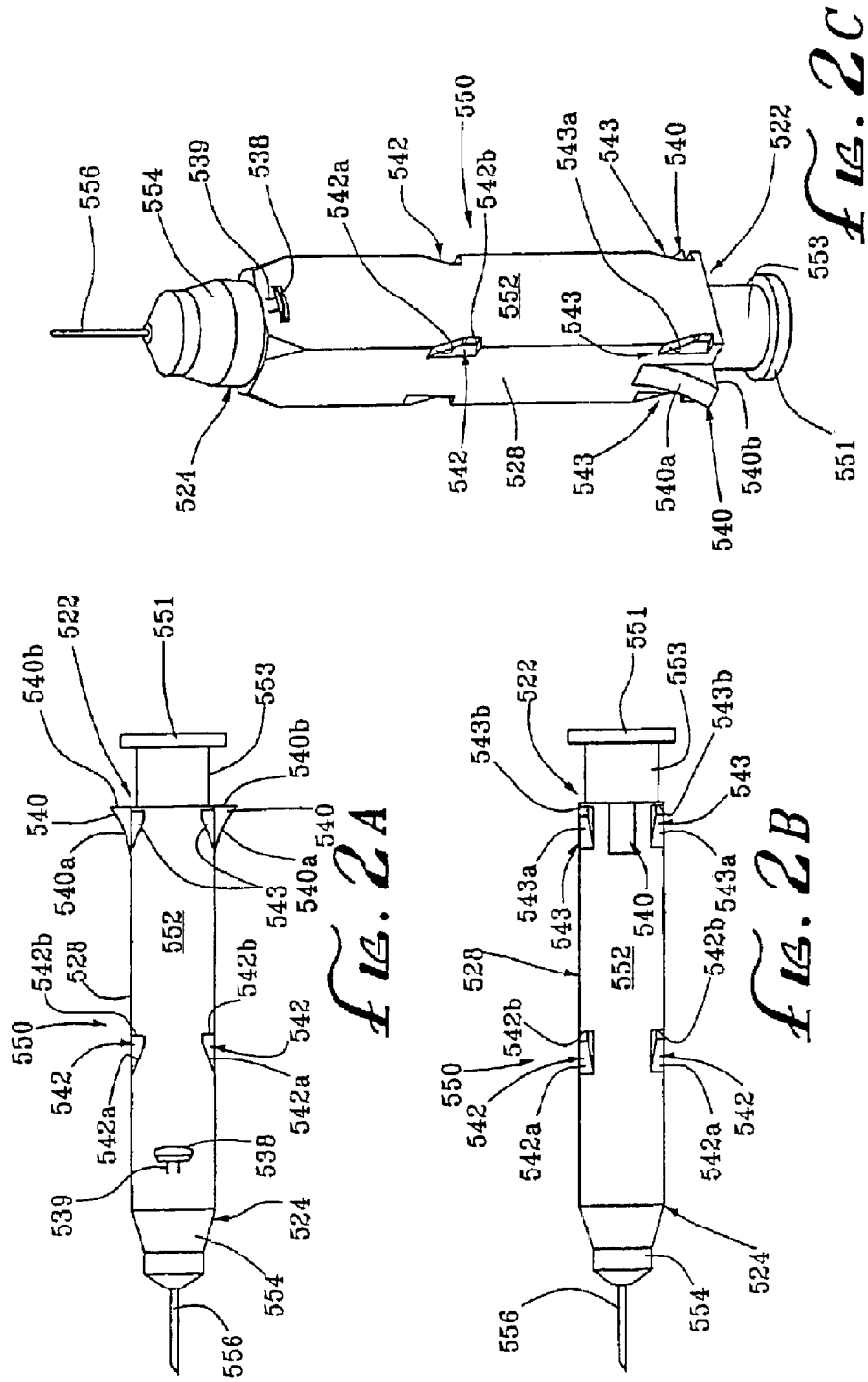

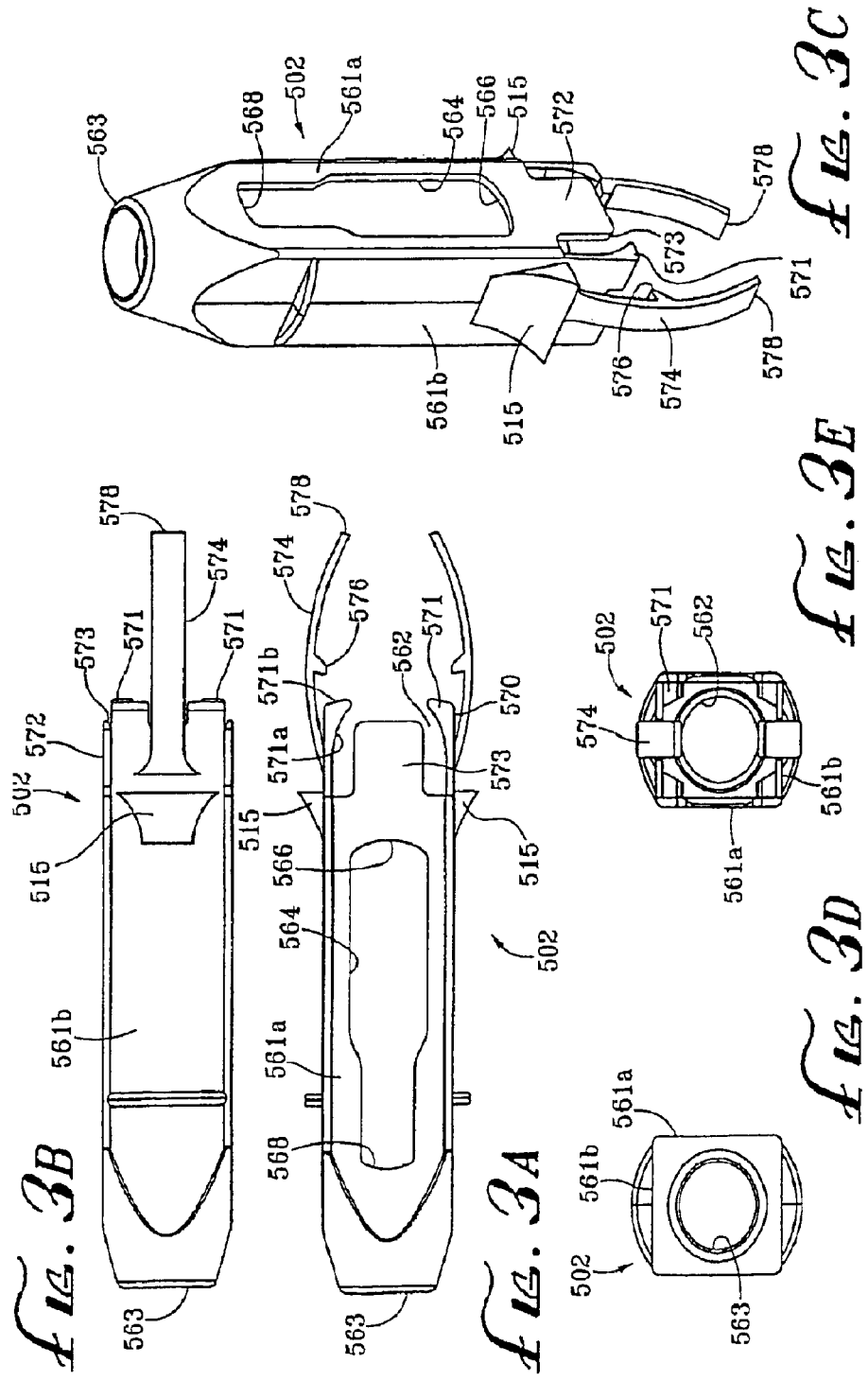

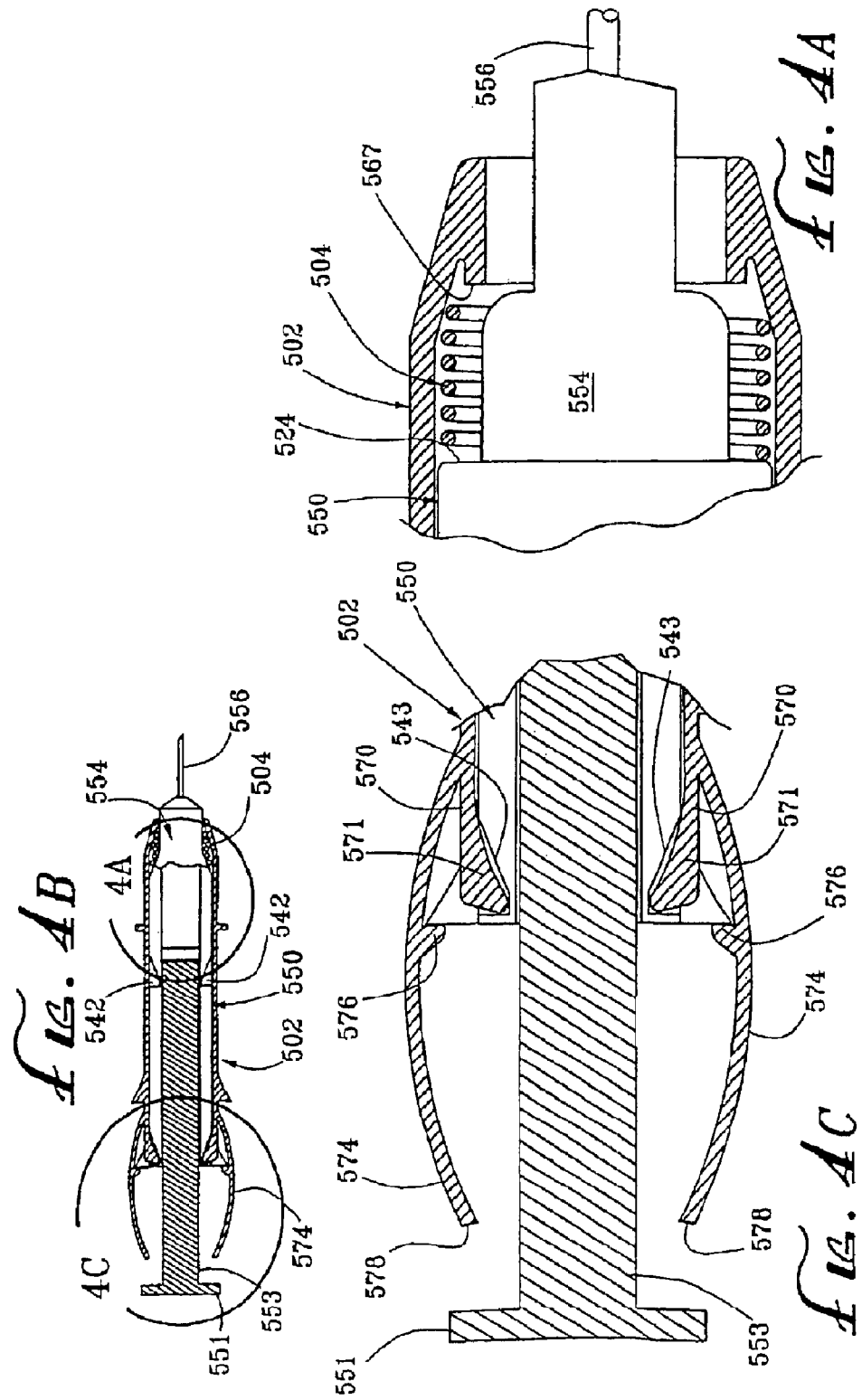

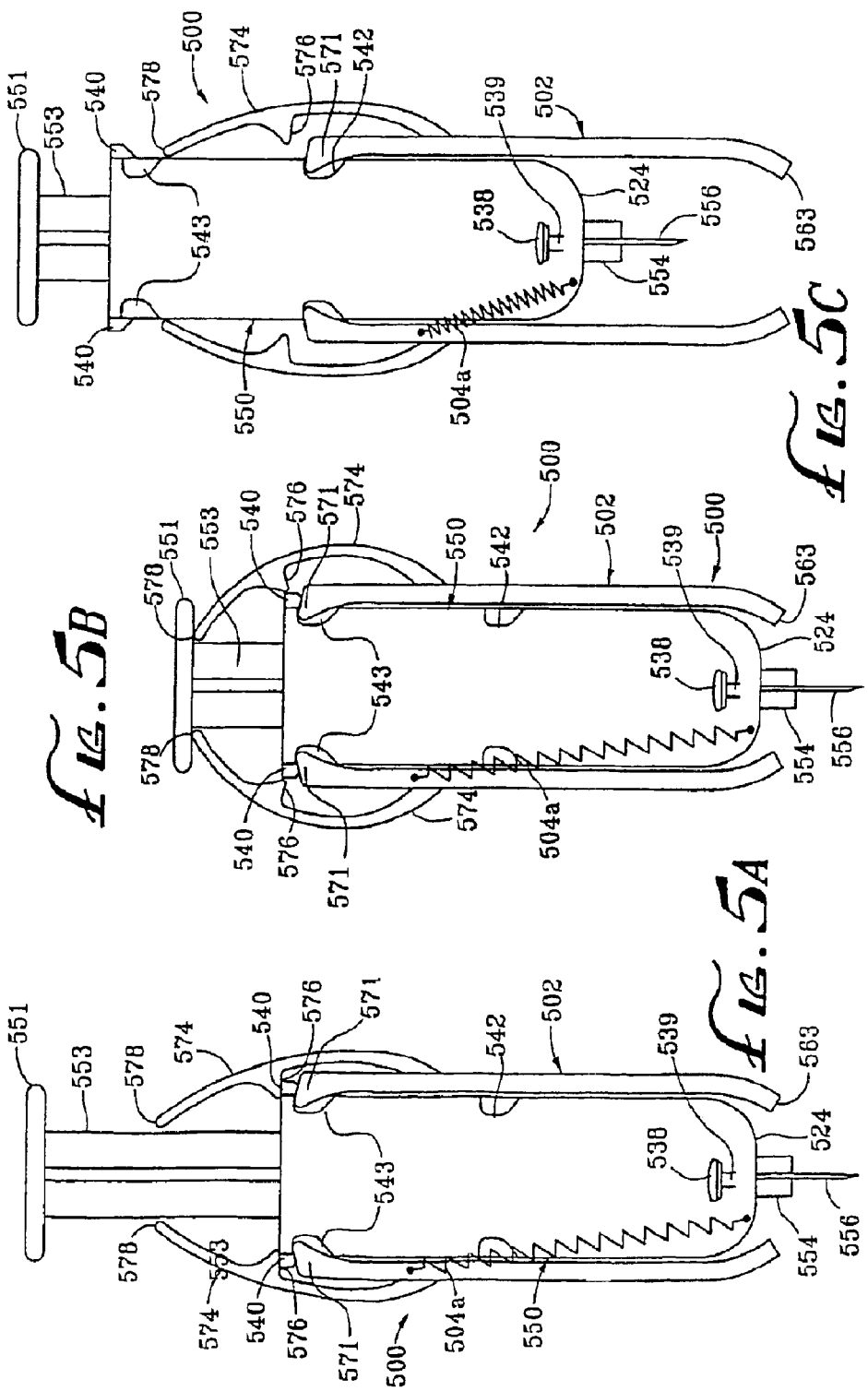

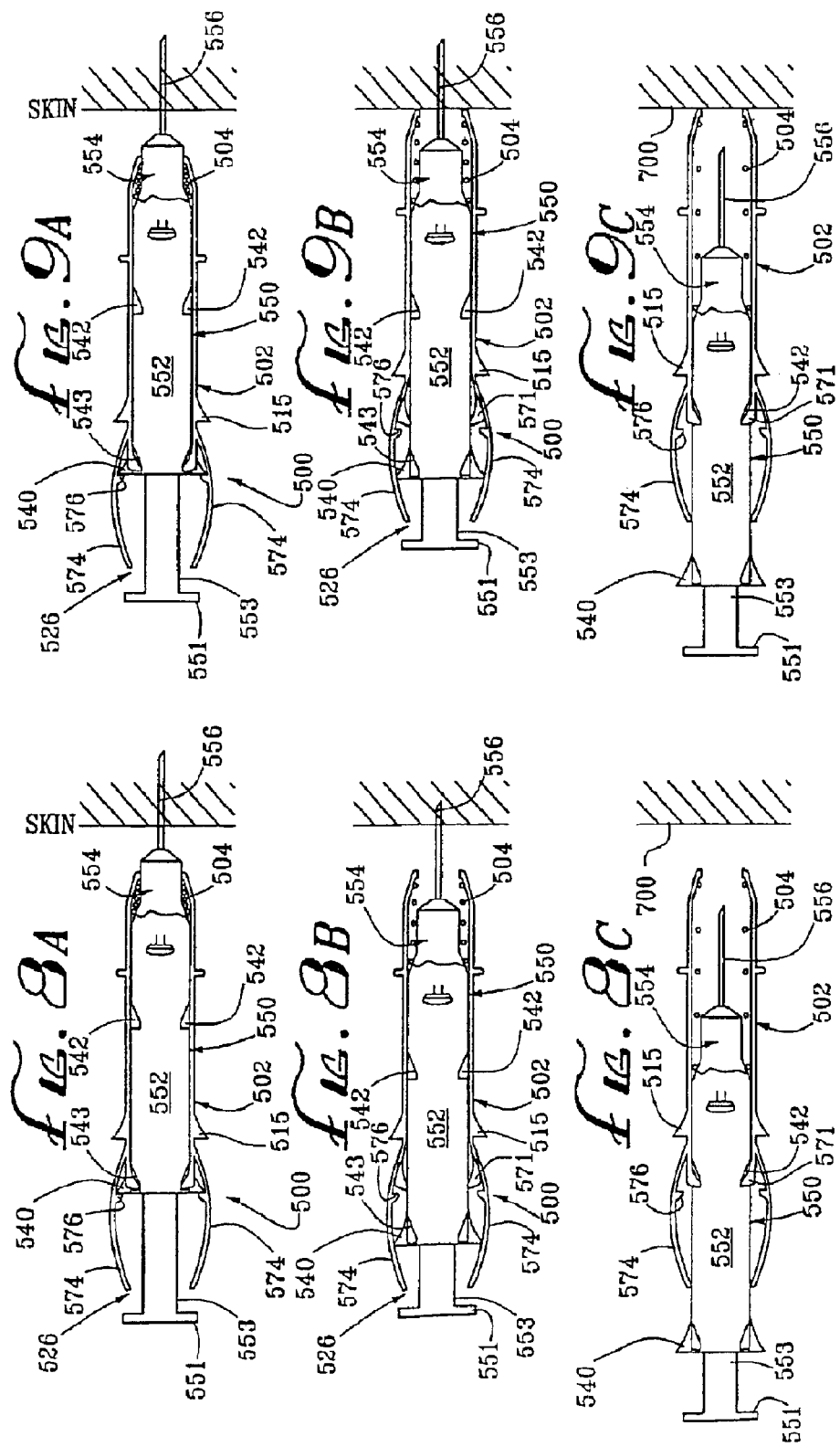

SYRINGE WITH NEEDLE GUARD INJECTION DEVICE

CROSS-REFERENCE TO RELATED APPLICATIONS

This application is a continuation of application Ser. No. 12/938,252 filed Nov. 2, 2010, now U.S. Pat. No. 8,241,255 which is a continuation of application Ser. No. 11/028,902 filed Jan. 3, 2005, now U.S. Pat. No. 7,824,379, which is a continuation of application Ser. No. 11/113,537 filed Mar. 27, 2002, now U.S. Pat. No. 6,976,976, which are fully incorporated herein by reference.

FIELD OF THE INVENTION

The present invention relates generally to injection devices for administering therapeutic agents to patients, particularly to safety devices for syringes, and more particularly to syringe devices that include a needle guard slidably coupled to a syringe for covering a needle of the syringe after use.

BACKGROUND

Medication is often dispensed using a medicine cartridge, such as a syringe, having a barrel with a needle extending from one end and a plunger slidably inserted into the other end. Such cartridges are often referred to as "pre-filled syringes" because they may contain a specific dosage or volume of medication when they are initially provided, as compared to conventional syringes that are furnished empty and filled by the user before making an injection.

Alternatively, a medicine cartridge may be used, such as an ampoule or vial, that includes a penetrable seal instead of a needle on one end of the barrel, and/or a piston rather than a plunger on the other end. Such medicine cartridges are generally inserted into an adapter that includes a hollow body adapted to hold the cartridge, a plunger to engage and move the piston in the cartridge, and/or a double-ended needle to penetrate the seal and communicate with the interior of the barrel.

Because of the risk of communicable diseases, a number of syringes and adapters have been developed that are intended to prevent accidental needle sticks and/or inadvertent reuse of a syringe. Retractable needle devices have been suggested for this purpose that include a cartridge that allows a needle of the cartridge to be withdrawn into the barrel after medication is dispensed from it. For example, U.S. Pat. No. 4,973,316 issued to Dysarz discloses a syringe including a barrel having a needle assembly that is slidable within the barrel between an exposed position such that a needle on the assembly extends from the barrel and a retracted position wherein the needle assembly is withdrawn into the barrel. The needle assembly is initially locked in the exposed position, but may be disengaged upon depression of the plunger, whereupon a spring biases the assembly towards the retracted position, thereby withdrawing the needle into the barrel.

Alternatively, syringe holders have been suggested that include a body within which a conventional syringe or cartridge may be received, and a shield that is manually slidable with respect to the body to cover the needle. For example, U.S. Pat. No. 6,030,366, issued to Mitchell, which is assigned to the assignee of the present application, discloses a self-shielding guard that includes a body having an open proximal end for inserting a syringe into a cavity within the body, and a distal end with an opening through which a needle on the syringe may extend once received in the body. A shield is slidable over the body between retracted and extended positions to expose and cover the needle, respectively. With the shield in the retracted position and the needle exposed, an injection may be made, and then the shield may be manually advanced to the extended position. In the extended position, cooperating detents and detent pockets on the body and shield substantially permanently lock together, thereby preventing reuse of the needle, reducing the risk of accidental needle sticks, and/or facilitating disposal of the syringe.

As an alternative to requiring manual extension of a shield to cover a needle, spring-loaded devices have also been suggested. These devices often include a body and slidable shield, similar to the manual devices described above, but also may include a spring element to bias the shield to advance and cover the needle. An actuator, such as a button or lever, may be activated by the user to release the shield, thereby allowing the spring element to advance the shield to cover the needle. For example, U.S. Pat. No. 5,695,475 issued to Best, Jr. et al. and U.S. Pat. No. 4,923,447 issued to Morgan disclose spring-loaded syringe devices that include inner and outer sliding sleeves that include a button slidable in a longitudinal slot to selectively expose and cover a needle on the devices. A spring in the devices biases one of the sleeves to extend and cover the needle, but this bias may be manually overcome to expose the needle. Thus, these devices may not lock the extending sleeve in a covered position, and therefore may risk accidental needle exposure and/or reuse of the needle. In addition, although these devices are spring-driven, their shields may not extend unless they are manually activated by using a button, and therefore are not truly "passive," but require an affirmative decision by a user to activate their safety feature.

Accordingly, an injection device that includes a needle shield for covering a needle after use would be useful.

SUMMARY OF THE INVENTION

The present invention is directed to injection devices incorporating both a syringe, such as a pre-filled syringe, or a medicine cartridge, and a guard that covers a needle of the syringe after a medication in the syringe is injected into a patient. The present invention is also directed to methods for making and using such injection devices.

In accordance with one aspect of the present invention, an injection device is provided that includes a syringe having a proximal end, a distal end, and a plunger extending from the proximal end. The injection device also includes a guard having a proximal end, a distal end, and a cavity therebetween. The guard is slidably mounted to the syringe and includes a latch member that extends proximally from the guard. A needle may extend from the distal end of the syringe. The guard is biased from a first or retracted position wherein the needle of the syringe is exposed, towards a second or extended position wherein the guard covers the needle. The guard may be biased by a spring element located in the distal portion of the guard and/or coupled to the syringe.

First cooperating detents on the syringe and the guard act to retain the guard in the first position. The first cooperating detents may include a ledge on the proximal end of the syringe and a catch on the latch member extending from the guard. Here, the ledge and detent engage one another to retain the guard in the first position. As the plunger is advanced within the syringe, the plunger may engage the latch member and release the first cooperating detents, whereupon the guard may slide towards the second position. Second cooperating detents may be provided on the syringe and guard to retain the guard in the second position. The second cooperating detents may include a detent on the guard and a corresponding detent pocket on the syringe.

Optionally, the guard may also include a window or slot that extends axially along the guard. When the slot is present on the guard, the syringe may include a stop tab configured to travel within the slot. The stop tab and slot may be configured to limit the proximal and distal movement of the syringe relative to the guard. For example, the stop tab may abut the distal edge of the slot or window when the guard is in the first position to prevent further distal movement of the syringe (or proximal movement of the guard). Similarly, the stop tab may abut the proximal edge of the slot when the guard is in the second position to prevent further proximal movement of the syringe (or distal movement of the guard). In addition, the guard may also include a set of finger flanges, grips, or protrusions usable for controlling the speed of advancement or sliding of the guard between the first and second positions.

In accordance with another aspect of the present invention, an injection device includes a guard having a proximal end and a distal end. The guard may be configured for slidably engaging a syringe, and may be biased between a first or retracted position and a second or extended position relative to the syringe, e.g., by a spring element. The injection device may also include a syringe having a proximal end, a distal end including a needle, and a plunger that extends from the proximal end. The needle may be coupled to the distal end of the syringe, i.e., molded to the distal end or a hub may be provided on the distal end of the syringe to which a needle may be attached, e.g., by threads or a luer lock. A latch member extends proximally from the guard that is detachably coupled with the syringe, thereby retaining the guard in the first position. The latch member is engageable by the plunger as the plunger is depressed for decoupling the latch member from the syringe. When the latch member is decoupled, the guard may be advanced from the first position towards the second position.

In a preferred embodiment, the latch member may include an intermediate portion that is engageable with a flange on the syringe, and a proximal portion that is engageable with the plunger as the plunger is advanced into the syringe. When the plunger engages the proximal portion of the latch member, the intermediate portion of the latch member may be deflected and released from the flange of the syringe. Additionally, cooperating detents on the guard and the syringe may secure the guard once the guard is advanced to the second position.

In accordance with yet another aspect of the present invention, a method is provided for delivering a therapeutic agent using an injection device. The injection device may include a guard having a proximal end, a distal end, and a latch member extending from the proximal end. The injection device may also include a syringe received in the guard including a needle extending from a distal end thereof, and a plunger extending from a proximal end thereof. The guard may be biased from a first position, wherein the needle is exposed, towards a second position, wherein the needle is covered by the guard.

Initially, the latch member may retain the guard in the first position. The needle may be inserted into a patient's skin while the user holds a portion of the injection device. A distal force may be applied to the plunger to inject the medication into the patient until the plunger contacts the latch member. The plunger may be depressed further to deflect the latch member, whereupon the guard may be released from the first position. The plunger may then be depressed yet further to complete delivery of the therapeutic agent. The user may then withdraw the needle from the patient's skin, and release the plunger, whereupon the syringe may retract proximally with respect to the guard until the needle is disposed within the guard. When the guard attains the second position, cooperating detents on the guard and the syringe may engage one another to lock the guard in the second position and/or prevent subsequent distal movement of the syringe relative to the guard.

Other objects and features of the present invention will become apparent from consideration of the following description taken in conjunction with the accompanying drawings.

BRIEF DESCRIPTION OF THE DRAWINGS

FIGS. 1A and 1B are side views of a preferred embodiment of an injection device, in accordance with the present invention.

FIGS. 2A and 2B are side views of a syringe for use in the injection device of FIGS. 1A and 1B.

FIG. 2C is a perspective view of the syringe of FIGS. 2A and 2B.

FIGS. 3A and 3B are side views of a guard for use in the injection device of FIGS. 1A and 1B.

FIG. 3C is a perspective views of the guard of FIGS. 3A and 3B.

FIGS. 3D and 3E are end views of the guard of FIGS. 3A and 3B, taken from distal and proximal ends of the guard, respectively.

FIG. 4A is a cross-sectional side view of the injection device of FIGS. 1A and 1B, with the guard in a retracted position relative to the syringe.

FIG. 4B is a detail of the proximal end of the injection device of FIG. 4A.

FIG. 4C is a detail of the distal end of the injection device of FIG. 4A.

FIGS. 5A-5C illustrate an alternative spring element for use with an injection device, in accordance with the present invention.

FIGS. 8A-8C illustrate one method of using an injection device of the present invention to perform an injection.

FIGS. 9A-9C illustrate another method of using an injection device of the present invention to perform an injection.

DETAILED DESCRIPTION

Figures 6A, 6B:
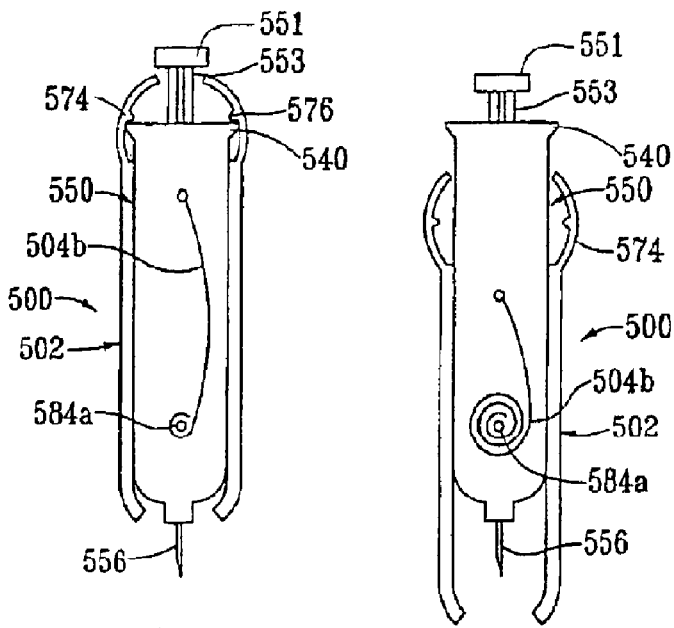
FIGS. 6A-6B illustrate another alternative spring element suitable for use with an injection device, in accordance with the present invention.
Figures 7A, 7B:
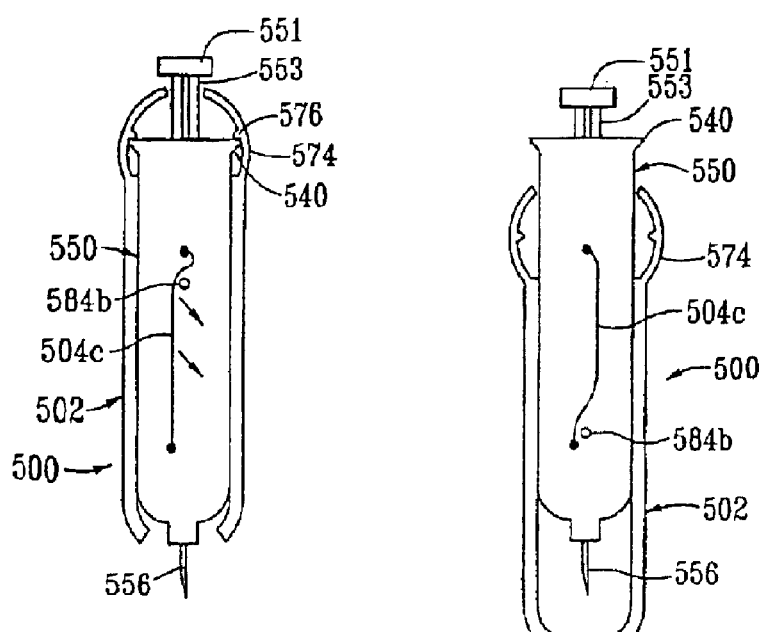
FIGS. 7A-7B illustrate yet another spring element that may be used with an injection device, in accordance with the present invention.

Turning to FIGS. 1A-4C, a preferred embodiment of an injection device 500 is shown for administering a medication, e.g., a vaccine, drug, or other therapeutic or diagnostic agent, to a patient. The device 500 includes a syringe 550 including a needle 556, and a guard 502 slidably attached to the syringe 550. The guard 502 is preferably biased from a first position wherein the needle 556 is exposed (shown in FIG. 1A) towards a second position wherein the guard 502 covers the needle 556 (shown in FIG. 1B).

As best seen in FIGS. 2A-2C, the syringe 550 includes a barrel 552, a distal end or hub 554 from which the needle 556 extends, and a plunger 553 inserted into a proximal end 522 of the barrel 552. In one embodiment, the needle 556 is attached to the hub 554 during manufacturing, and the device 500 is provided to a user with the needle 556 pre-attached. In another embodiment, the hub 554 includes a connector, e.g., a thread or luer lock adaptor. Thus, the device 500 may be provided to a user without a pre-attached needle 556, and the user may attach a desired needle 556 to the hub 554 before use.

Although a substantially square cross-section is shown, the barrel 552 may have a substantially cylindrical cross-section, rectangular cross-section, or other suitably shaped cross-section. As illustrated, one or more stop tabs 538 may be provided on the barrel 552. The stop tabs 538 extend transversely outwardly, e.g., on opposite sides of the barrel 552. The plunger 553 may include a thumb pad 551 on its proximal end to move the plunger 553 axially within the barrel 552. The thumb pad 551 may have a diameter or other cross-section that is larger than a diameter of the barrel 552 of the syringe 550. In addition, or alternatively, the plunger 553 may include an intermediate tab (not shown) located distally to the thumb pad 551.

In the illustrated embodiment, one or more sets of ledges 540 may be provided, e.g., molded, on or near the proximal end 522 and on one or more side walls of the syringe 550. Preferably, each ledge 540 has a sloping distal edge 540a and a substantially blunt proximal edge 540b defining a detent pocket adjacent the proximal edge 540b.

In addition, the syringe 550 may include one or more sets of detent pockets 542, 543 adjacent the ledges 540. A proximal set of detent pockets 543 may have substantially blunt proximal edge 543b and sloping or substantially blunt distal edges 543a. A distal set of detent pockets 542 may be provided at a location on the syringe 550 distal to the ledges 540 and/or adjacent the distal end 554 of the syringe 550. Similar to the proximal detent pockets 543, the distal detent pockets 542 may have substantially blunt proximal edges 542b and have sloping or substantially blunt distal edges 542a.

Turning to FIGS. 3A-3E, the guard 502 is a tubular member having an inner cross-section configured to slidably fit on the syringe 550. For example, the inner cross-section of the guard 502 may be substantially rectangular, square, or cylindrical in cross-section, depending upon the cross-section of the syringe 550. The guard 502 includes one or more side walls 561a, 561b, an open proximal end 562, and an open distal end 563 defining a passage therebetween. Assembly tabs 572 with sloping or ramped interior surfaces 573 may be molded into and extend proximally from the side walls 561a. Optionally, at least one side wall 561a, e.g., opposing walls 561a, may include an elongate opening or slot 564 therethrough for receiving the stop tabs 538 and/or for facilitating observation of the syringe 550 received in the guard 502. A pair of finger grips 515 may be located on the guard 502, e.g., on opposite side walls 561b.

One or more latch members or fingers 574 extend proximally from the guard 502, e.g., molded to the side wall(s) 561b. Each latch member 574 includes an inwardly disposed catch or tab 576 located on an intermediate portion of the latch member 574 between the assembly tab 572 and a proximal tip 578 of the latch member 574. The catches 576 and the ledges 540 may provide a set of cooperating detents for retaining the guard 502 in the first position. Alternatively, in embodiments where the syringe 550 lacks the ledges 540 (not shown), the catches 576 may engage with a flange on the proximal end 522 of the syringe 550, or may engage the proximal end 522 itself, thereby defining a proximal set of cooperating detents that retain the guard 502 in the first position. Preferably, the latch members 574 are substantially flexible or semi-rigid, and may be curved such that the intermediate portions are disposed radially outwardly further than the proximal tips 578 when the latch members 574 are in a relaxed, unstressed state. Thus, if the proximal tips 578 are directed distally, the latch members 574 may partially bend or bow, thereby directing the intermediate portions, and consequently the catches 576, transversely outwardly.

A plurality of detent arms 570 and a plurality of detents 571 are provided on the guard 502, preferably molded directly to the side walls 561b. The detents 571 preferably have shapes corresponding substantially to the shapes of the distal detent pockets 542 in the syringe 550. For example, distal edges 571a of the detents 571 may be ramped to facilitate slidable engagement with the proximal detent pockets 543 in the syringe 550. Proximal edges 571b of the detents 571 are substantially blunt for positively engaging the proximal edges 542b of the distal detent pockets 542 and locking the guard 502 in the second position. Together, the detents 571 and distal detent pockets 542 at least partially define a second set of cooperating detents for securing the guard 502 in the second position.

As best seen in FIGS. 1B, 4A, and 4C, the injection device 500 may include a spring element 504 for biasing the guard 502 towards the second position. The syringe 550 may include a substantially blunt distal surface 525 that is proximal from the hub 554, and the guard 502 may include a substantially blunt inner collar 567. The spring 502 may be positioned concentrically within the guard 502 such that respective ends of the spring 504 engage the distal surface 525 and the inner collar 567. Thus, the guard 502 and syringe 550 together at least partially define an annular space within which the compression spring 504 may be compressed when the guard 502 is in the first position. Alternatively, other configurations may be provided for the spring element 504, such as those shown in FIGS. 5A-7B, and described further below.

The injection device 500 is pre-assembled such that the guard 502 is disposed in the first position, as illustrated in FIG. 1A. In the first position, the catches 576 on the latch members 574 may engage the ledges 540 of the syringe 550 to retain the guard 502 in the first position. Specifically, the catches 576 on the latch members 574 engage the proximal edges 540b of the ledges 540 on the syringe 550, as seen in FIG. 1A, thereby retaining the guard 502 in the first position. In embodiments of the injection device 500 that lack the ledges 540, the catches 576 may directly engage the proximal end 522 of the syringe 550 or a flange (not shown) on the syringe 550. Optionally, in the first position, stop tabs 538 on the syringe 550 may abut the distal edge 568 of slots or windows 564 in the guard 502, as shown in FIG. 1A. Additional information on assembling the guard 502 and the syringe 550, may be found in co-pending application Ser. No. 09/724,657, filed Nov. 28, 2000, the disclosure of which is expressly incorporated herein by reference.

Once assembled with the guard 502 in the first position, the injection device 500 may be used to inject medication from the barrel 552 into a patient (not shown). A needle cover (not shown) may be removed from the needle 556, and the needle 556 inserted into the patient. Medication may then be delivered by directing the plunger 553 distally with the user's thumb until the thumb pad 551 contacts the tips 578 of the latch members 574. While using the injection device 500, the user preferably places a finger on each finger grip 515 and the thumb on the thumb pad 551. As the plunger 553 is depressed further, the thumb pad 551 may cause the latch members 574 to compress axially, thereby deflecting the intermediate portions radially outwardly until the catches 576 are disengaged from the ledges 540 on the syringe 550.

With the ledges 540 and catches 576 disengaged, the spring element 504 automatically biases the guard 502 distally towards the second position, i.e., to advance the distal end 563 of the guard 502 over the needle 556. The syringe 550 may be maintained substantially stationary relative to the patient's skin, and the plunger 553 may be depressed further, if necessary, to complete the injection. When the catches 576 are disengaged, the guard 502 may advance until it contacts the patient's skin, and the needle 556 may be withdrawn from the patient, allowing the guard 502 to extend entirely over the needle 556. As the guard 502 advances, the latch members 574 may slide distally along the syringe 550.

When the needle 556 is withdrawn from the patient, the guard 502 may advance fully to the second position such that the guard 502 passes over and substantially covers the needle 556. In the second position, shown in FIG. 4A, the detents 571 of the guard 502 enter and substantially engage the distal detent pockets 542 of the syringe 550, thereby preventing subsequent proximal movement of the guard 502. Stop tabs 538 on the syringe may also abut the proximal edges 566 of the slots 564, thereby preventing further distal movement of the guard 502. Thus, the guard 502 may be substantially permanently locked in the second or extended position, thereby preventing reuse of the injection device 500 and/or facilitating safe disposal of the injection device 500.

In the second position, the spring element 504 may remain slightly compressed to provide a distal force that may ensure that the guard 502 is fully advanced and the detents 571 are received in the distal detent pockets 542.

In further alternatives, additional elements may be provided on the syringe 550 and/or guard 502 to control the speed of advancement of the guard 502 from its initial activation in the retracted position, but allow free advancement as the guard 502 approaches the extended position. For example, a frictional material (not shown) may be applied to one or more contact surfaces between the syringe 550 and guard 502 that may increase the frictional resistance in the retracted position. An adhesive tape or viscous material (not shown) may be provided that peels off of, is cut or torn, or otherwise separates from the syringe 550 and/or guard 502 after partial advancement of the guard 502. One or more "speed bumps" or similar protruding structures (not shown) may be molded into or otherwise provided on the syringe 550 and/or guard 502 that may be contacted when the guard 502 is in or close to the retracted position. A feature on one of the syringe 550 or guard 502 may travel through a corresponding tortuous feature on the other of the syringe 550 or guard 502 to slow the guard 502 down initially. In a further alternative, a spring or cushioned pad (not shown) may be provided on the distal end of the guard 502 that may soften the force with which the guard 502 contacts the patient if the guard 502 is allowed to advance.

In the embodiment described above, the spring element 504 is a helical compression spring. Alternatively, one or more springs (not shown) may be provided, e.g., in one or more corners of the guard 502. For example, springs may be provided in diagonally opposite corners of the guard 502 in order to minimize the risk of subjecting the syringe 550 to torque as it advances from the retracted towards the extended position as may occur if only a single off-center spring is used. In another alternative, one or more helical extension springs 504a may be provided that have respective ends that are secured to the syringe 550 and the guard 502, as is shown schematically in FIGS. 5A-5C. The extension spring 504a may be provided between the guard 502 and the syringe 550. The extension spring 504a may be under tension when the guard 502 is disposed in the retracted position, thereby biasing the guard 502 towards the extended position.

Other alternative spring elements may also be provided that may be coupled to the guard 502 and syringe 550. FIGS. 6A and 6B illustrate an embodiment of the present invention having a coil spring element 504b that has one end mounted around a hub 584a on the guard 502 (attachment point of hub 584a to the guard 502 not shown) and the other end secured to the syringe 550. The coil spring element 504b may unwind as the guard 502 is retracted to the retracted position, as in FIG. 6A, but is biased to wind back around the hub 584a to advance the guard 502 towards the extended position, which is shown in FIG. 6B. In another alternative, illustrated in FIGS. 7A and 7B, a leaf spring element 504c may be provided that has ends fixed to one of the guard 502 and the syringe 550 for distally biasing a hub 584b coupled to the other of the syringe 550 and the guard 502 (attached point of hub 584b to body 502 not shown). The guard 502 may be retracted, thereby deflecting the leaf spring element 504c, as in FIG. 7A, but when the guard 502 is released, the hub 584b and consequently the guard 502 may be advanced to the extended position as the leaf spring element 504c attempts to return to its relaxed, undeflected state, as in FIG. 7B.

In addition, if desired, any of the spring elements 504-504c may have a nonlinear spring rate, preferably having a spring rate when the guard 502 is disposed in the retracted position that is substantially more or less than its spring rate when the guard 502 approaches the extended position. A nonlinear spring rate may be useful to provide an injection device 500 that is "softer" upon activation, i.e., such that the spring element (504-504c) may apply a substantially lower force to the guard 502 when it is initially released from the retracted position than when it approaches the final extended position. For example, the thickness of the spring material may be varied along its length, different materials may be used for different portions of the spring, and the like. This "softer" spring may minimize the force with which the guard 502 contacts a patient being injecting using the injection device 500, and thereby reduce the discomfort or anxiety that may be experienced by the patient. For example, the guard 502 may be activated with a softer force, such that the guard 502 more gently contacts the patient, but when the needle is withdrawn from the patient, a stronger force may be applied to the guard 502 to ensure that it advances completely to the extended position.

Turning to FIGS. 8A-8C, another method is shown for performing an injection using an injection device 500. Unlike the previous embodiments, which generally discuss a guard advancing over a syringe, this method involves holding the guard 502 such that the syringe 550 may be automatically and/or controllably directed proximally to retract the needle 556 into the guard 502. The guard 502 and syringe 550 are slidably attached to each other, similar to the previous embodiment. The guard 502 includes a spring element 504, similar to the previous embodiments, for biasing the syringe 550 towards a second position wherein the guard 502 substantially covers the needle 556.

As best seen in FIG. 8A, a needle cover (not shown) may be removed from the needle 556, and the needle 556 may be inserted into a patient's skin 700. A user may grasp finger grips 515 or otherwise grip an outer surface of the guard 502. Thus, the guard 502 may be grasped to hold the injection device 500 substantially stationary with respect to the skin 700 during the injection.

To deliver medication from the syringe 550, the user may grip the finger grips 515 and apply a distal force to the plunger 553, preferably until thumb pad 551 engages latch members 574 extending from the guard 502. As the plunger 553 is depressed further, the thumb pad 551 may cause the latch members 574 to compress axially and thereby deflect radially outwardly until the catches 576 (not shown in FIGS. 8A-8C)

are disengaged from the ledges 540 (also not shown) of the syringe 550, or are disengaged from the proximal end 522 if the syringe 550 does not include the ledges 540. With the catches 576 disengaged, the spring element 504 may automatically bias the syringe 550 towards the second or retracted position, shown in FIG. 8C.

Once the ledges 540 or the proximal end 522 are disengaged from the catches 576, the user may gradually remove the distal force applied to the plunger 553, allowing a controlled retraction of the syringe 550 to the retracted position. As the syringe 550 retracts to the retracted position, the guard 502 may remain substantially stationary with respect to the patient's skin 700, and the needle 556 may be withdrawn from the patient and into the guard 502, as shown in FIGS. 8B and 8C. Once in the fully retracted position, cooperating detents 571, 542 on the guard 502 and syringe 550 engage one another to substantially and permanently lock the guard 502 over the needle 556. Thus, the user may hold the finger grips 515 to position the injection device 500 a predetermined distance way from the patient's skin 700, thereby avoiding any sudden contact between the guard 502 and the patient's skin 700 when the ledges 540, or proximal end 522, of the syringe 550 and the catches 576 are disengaged.

Alternatively, as shown in FIGS. 9A-9C, the user may hold the injection device 500 using finger grips 515, insert the needle 556 into the patient's skin 700, and then inject medication by applying a distal force to the plunger 553 until the thumb pad 551 engages a latch member 574 extending from the guard 502. As described above, further depression of the plunger 553 deflects the latch member 574 to disengage the catches 576, and release the guard 502. The guard 502 may then automatically advance into contact with the patient's skin 700, as shown in FIG. 9B. The plunger 553 may be further advanced to complete the injection. Preferably, because the spring element 504 is not fully expanded, the syringe 550 remains biased to retract with respect to the guard 502 towards the retracted position. At this point, the user may gradually remove the distal force applied to the plunger 553, allowing controlled retraction of the syringe 550 to the retracted position, as shown in FIG. 9C. Once the syringe 550 retracts to the retracted position, the cooperating detents 571, 542 may engage one another to substantially permanently lock the guard 502 over the needle 556, similar to the embodiment discussed above.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A method for delivering a therapeutic agent using an injection device including a guard comprising a proximal end, a distal end, and a latch member extending from the guard, and a syringe slidably received in the guard, the syringe comprising a proximal end, a distal end, a needle extending from the distal end, and a plunger extending from the proximal end, the syringe being biased to move relative to the guard from a first position wherein the needle is exposed beyond the distal end of the guard towards a second position wherein the needle is disposed within the guard, the latch member retaining the guard in the first position, the method comprising:

inserting the needle into a patient;
depressing the plunger through an injection stroke to inject the therapeutic agent into the patient until the plunger at least disengages the latch member during the injection stroke, whereupon the syringe is free to move from the first position;
releasing the plunger, whereupon the syringe automatically withdraws proximally within the guard towards the second position,
wherein the syringe further comprises proximal and distal pockets;
wherein the syringe and guard further comprises first cooperating detents for retaining the guard in the first position; and
wherein the guard further comprises second cooperating detents for engaging the syringe pockets for retaining the guard in the first and second positions.

2. The method of claim 1, wherein the second cooperating detents engaging the syringe pockets retaining the guard in the second position to prevent subsequent movement of the guard with respect to the syringe.

3. The method of claim 1, wherein the guard further comprises a set of finger grips, and wherein the releasing step comprises holding the finger grips and the plunger to controllably release the plunger, thereby controlling a speed at which the syringe is moved towards the second position.

4. The method of claim 1, wherein the needle is withdrawn from the patient, as the syringe is retracted towards the second position.

5. The method of claim 1, wherein the needle is withdrawn into the guard as the syringe is retracted towards the second position.

6. The method of claim 1, wherein the latch member comprises a finger extending from the guard towards the plunger, the finger being deflected radially outward to disengage a catch thereon from a mating catch on the syringe when the plunger is depressed.

7. The method of claim 1, further comprising a spring coupled to the guard and the syringe, the spring biasing the syringe toward the second position.

8. A method for delivering a therapeutic agent using an injection device including a guard comprising a proximal end, a distal end, and a latch member extending from the guard, and a syringe slidably received in the guard, the syringe comprising a proximal end, a distal end, a needle extending from the distal end, and a plunger extending from the proximal end, the syringe being biased to move relative to the guard from a first position wherein the needle is exposed beyond the distal end of the guard towards a second position wherein the needle is disposed within the guard, the latch member retaining the guard in the first position, wherein the guard and the syringe further comprise cooperating detents and detent pockets, and wherein the cooperating detents and detent pockets engage one another when the syringe is in the second position to prevent subsequent movement of the syringe with respect to the guard, the method comprising:

inserting the needle into a patient;
depressing the plunger through an injection stroke to inject the therapeutic agent into the patient until the plunger at least disengages the latch member during the injection stroke, whereupon the syringe is free to move from the first position;
releasing the plunger, whereupon the syringe automatically withdraws proximally within the guard towards the second position, and retaining the guard in the second position by engaging detent pockets on the syringe with cooperating detents on the guard.

* * * * *